United States Patent
Almendinger et al.

(10) Patent No.: US 7,610,099 B2
(45) Date of Patent: Oct. 27, 2009

(54) METHOD OF PROCESSING TELEMETRY SIGNALS IN AN IMPLANTABLE MEDICAL DEVICE INCLUDING A TELEMETRY PROCESSOR

(75) Inventors: Allen Dale Almendinger, Bloomington, MN (US); Martinus A G M Bakx, Geleen (NL)

(73) Assignee: Medtronic, Inc., Minneapolis, MN (US)

(*) Notice: Subject to any disclaimer, the term of this patent is extended or adjusted under 35 U.S.C. 154(b) by 497 days.

(21) Appl. No.: 11/463,782

(22) Filed: Aug. 10, 2006

(65) Prior Publication Data

US 2006/0287694 A1    Dec. 21, 2006

Related U.S. Application Data

(62) Division of application No. 10/657,047, filed on Sep. 5, 2003, now Pat. No. 7,254,448, which is a division of application No. 09/595,971, filed on Jun. 19, 2000, now Pat. No. 6,738,670.

(51) Int. Cl.
    *A61N 1/08* (2006.01)
(52) U.S. Cl. .............................. 607/60; 607/16; 607/31
(58) Field of Classification Search ........................ None
    See application file for complete search history.

(56) References Cited

U.S. PATENT DOCUMENTS

| | | | |
|---|---|---|---|
| 4,267,843 A | | 5/1981 | McDonald |
| 4,562,841 A | * | 1/1986 | Brockway et al. ............. 607/29 |
| 4,980,898 A | | 12/1990 | Silvian |
| 5,127,404 A | | 7/1992 | Wyborny |
| 5,186,169 A | | 2/1993 | Schaldach |
| 5,292,343 A | | 3/1994 | Blanchette |
| 5,314,450 A | | 5/1994 | Thompson |
| 5,342,408 A | | 8/1994 | DeCoriolis |
| 5,350,411 A | * | 9/1994 | Ryan et al. .................... 607/32 |
| 5,354,319 A | | 10/1994 | Wyborny |
| 5,383,912 A | | 1/1995 | Cox |
| 5,383,915 A | | 1/1995 | Adams |
| 5,466,246 A | | 11/1995 | Silvian |
| 5,522,866 A | | 6/1996 | Fernald |
| 5,728,154 A | | 3/1998 | Crossett |
| 5,741,315 A | | 4/1998 | Lee |
| 5,774,501 A | | 6/1998 | Halpern |
| 5,891,184 A | | 4/1999 | Lee |
| 5,919,214 A | | 7/1999 | Ciciarelli |
| 5,935,078 A | | 8/1999 | Feierbach |
| 5,978,713 A | | 11/1999 | Prutchi |
| 5,999,857 A | | 12/1999 | Weijand |

(Continued)

FOREIGN PATENT DOCUMENTS

EP    0 695 558 A2    2/1996

*Primary Examiner*—Kennedy J Schaetzle
(74) *Attorney, Agent, or Firm*—John W. Albrecht (57) ABSTRACT

An implantable medical device with a main processor also has a telemetry processor to perform some telemetry processing functions resulting under some circumstances in reducing demands on the main processor, conserving energy, increasing telemetry processing speed, and many other advantages. A wide variety of implantable medical devices can be configured with a telemetry processor including neuro stimulators, pacemakers, defibrillators, drug delivery pumps, diagnostic recorders, and cochlear implants. The telemetry processor includes control logic, a data decoder, a receive buffer, a data encoder, and a transmit buffer. Methods of receiving messages and transmitting messages with a telemetry processor are also disclosed.

5 Claims, 12 Drawing Sheets

U.S. PATENT DOCUMENTS

| | | |
|---|---|---|
| 6,073,050 A | 6/2000 | Griffith |
| 6,106,551 A | 8/2000 | Crossett |
| 6,141,592 A | 10/2000 | Pauly |
| 6,167,310 A | 12/2000 | Grevious |
| 6,292,698 B1 | 9/2001 | Duffin |
| 6,295,473 B1 | 9/2001 | Rosar |
| 6,298,271 B1 | 10/2001 | Weijand |
| 6,434,429 B1 | 8/2002 | Kraus |
| 6,441,747 B1 | 8/2002 | Khair |
| 6,453,200 B1 | 9/2002 | Koslar |
| 6,470,215 B1 | 10/2002 | Kraus |
| 6,490,487 B1 | 12/2002 | Kraus |
| 6,507,759 B1 | 1/2003 | Prutchi |
| 2002/0082665 A1 | 6/2002 | Haller |
| 2002/0173830 A1 | 11/2002 | Starkweather |
| 2003/0009203 A1* | 1/2003 | Lebel et al. .......... 607/60 |

* cited by examiner

METHOD OF PROCESSING TELEMETRY SIGNALS IN AN IMPLANTABLE MEDICAL DEVICE INCLUDING A TELEMETRY PROCESSOR

CROSS-REFERENCE

The present application is a divisional of application Ser. No. 10/657,047, filed Sep. 5, 2003, now U.S. Pat. No. 7,254,448 issued on Aug. 7, 2007; which is a divisional of application Ser. No. 09/595,971, filed Jun. 19, 2000, now U.S. Pat. No. 6,738,670 issued on May 18, 2004, for which priority is claimed. The parent application is incorporated herein by reference in its entirety.

In addition, the present application is related to U.S. Pat. No. 6,453,198 entitled "Power Management For An Implantable Medical Device" which is not admitted as prior art with respect to the present invention by its mention in this cross-reference section.

BACKGROUND OF THE INVENTION

This disclosure relates to a medical device and more specifically to an implantable medical device capable of telemetry.

The medical device industry produces a wide variety of electronic and mechanical devices for treating patient medical conditions. Depending upon medical condition, medical devices can be surgically implanted or connected externally to the patient receiving treatment. Clinicians use medical devices alone or in combination with drug therapies and surgery to treat patient medical conditions. For some medical conditions, medical devices provide the best, and sometimes the only, therapy to restore an individual to a more healthful condition and a fuller life. Many implantable medical devices have the capability for telemetry so once implanted communications can be conducted with the medical device.

Implantable medical devices that can have telemetry capability typically include neuro stimulators, pacemakers, defibrillators, drug delivery pumps, and diagnostic recorders. Telemetry is typically conducted with a telemetry signal at a frequency in the range from about 150 KHz to 200 KHz using a medical device protocol such as described in U.S. Pat. No. 5,752,977 "Efficient High Data Rate Telemetry Format For Implanted Medical Device" issued to Grevious et al. (May 19, 1998). As medical device telemetry has become more complex, the telemetry has placed greater demands on the medical device processor. Also as implantable medical devices therapies have become more complex, more demands have been placed on the medical device processor. The competing demands of telemetry and therapies for medical device processor capability can place constraints on the operation of the medical device and can consume more power than desired.

For the foregoing reasons there is a need for an implantable medical device to be configured with some telemetry functions independent of the main processor to free the main processor for other functions, conserve energy, increase telemetry processing speed, and to provide many other advantages.

SUMMARY OF THE INVENTION

An implantable medical device telemetry processor performs some telemetry processing functions that under some circumstances result in reducing demands on the main processor to free the main processor for other tasks, conserving energy, increasing telemetry processing speed, and many other advantages. The telemetry processor includes control logic, a data decoder, a receive buffer, a data encoder, and a transmit buffer. The control logic operates the telemetry processor according to instructions. The data decoder is coupled to the control logic and coupleable to a demodulator, and the data decoder translates a received serial bit stream into parallel accessible words. The receive buffer is coupled to the data decoder and coupleable to a main processor bus. The data encoder is coupled to the control logic and coupleable to a modulator, and the data encoder translates parallel accessible words into a transmit serial bit stream. The transmit buffer is coupled to the data encoder and coupleable to the main processor bus.

DETAILED DESCRIPTION OF THE PREFERRED EMBODIMENTS

Figure 1:
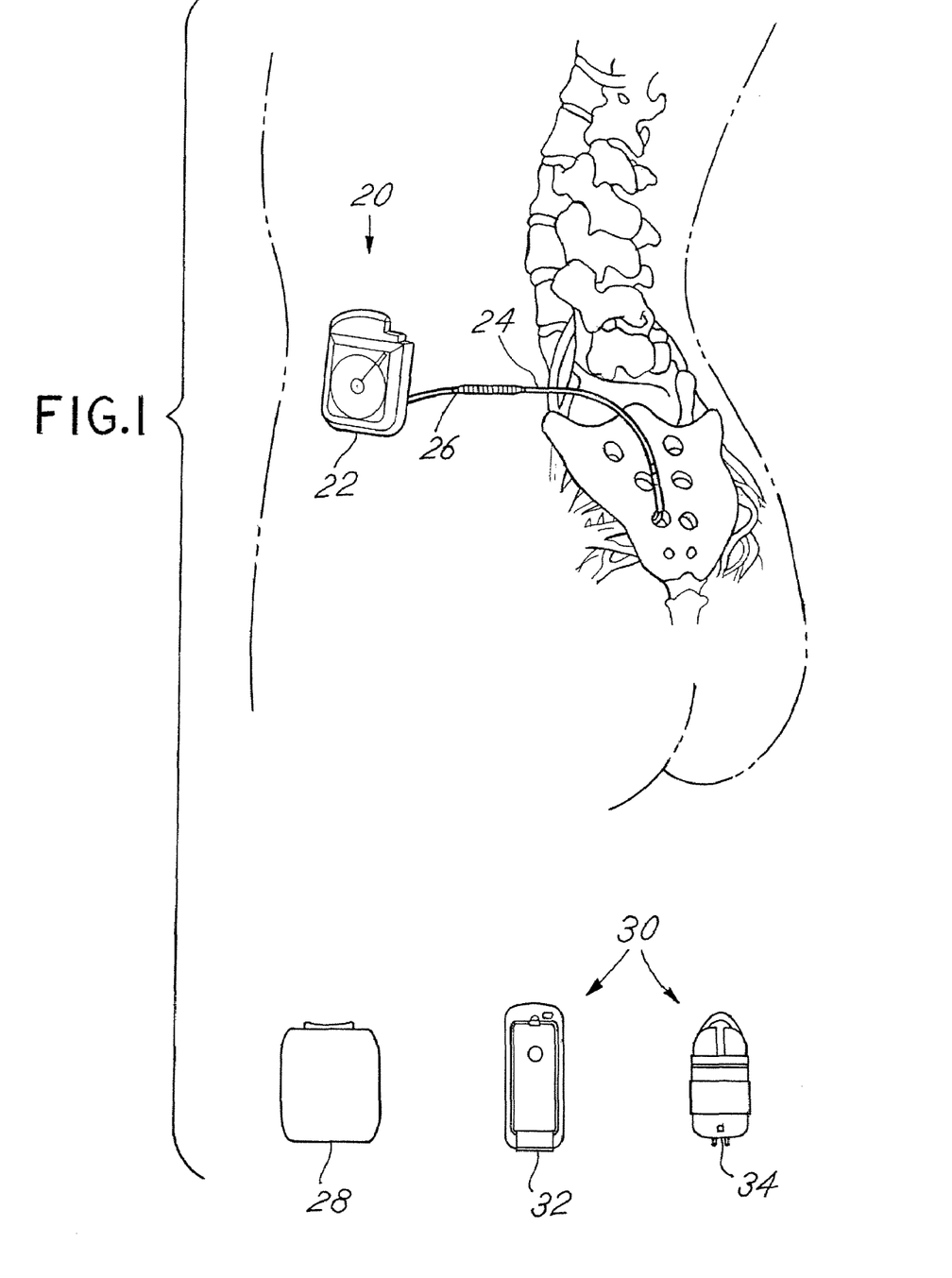
FIG. 1 shows an environment of an implantable medical device embodiment.

FIG. 1 shows the general environment of an implantable medical device 20 and more specifically an Implantable Neuro Stimulator (INS) 22 embodiment that includes a stimulation lead 24, a lead extension 26, an External Neuro Stimulator (ENS) 28, and programmers 30 including a physician programmer 32, and a patient programmer 34 embodiments. Although a INS 22 embodiment is shown, the implantable medical device 20 could also include pacemakers, defibrillators, drug delivery pumps, diagnostic recorders, cochlear implants, and the like. The implantable medical device 20 is typically programmed with a therapy and then implanted in the body typically in a subcutaneous pocket at a site selected after considering clinician and patient preferences. A wide variety of programmers 30, also known as downlink transmitters, can be used to transmit data to and receive data from the implantable medical device 20, also known as the uplink transmitter. Examples of downlink transmitters include devices such as physician programmers 32, patient programmers 34, programming wands, telemetry access units, and the like. The clinician periodically uses a physician programmer 32 to communicate with the implantable medical device 20 to manage the patient's therapy and collect implantable medical device 20 data. The patient uses the patient programmer 34 to communicate with the implanted INS 22 to make therapy adjustments that have been programmed by the clinician. Both the physician programmer 32 and patient programmer 34 can have an antenna locator that indicates when the telemetry head is aligned closely enough with the implanted INS 22 for adequate telemetry. An example of a physician programmer 32 is a Model 7432 Console Programmer available from Medtronic, and an example of a patient programmer 34 is a Model 7434 Itrel® 3 EZ Patient Programmer available from Medtronic.

Figure 2:
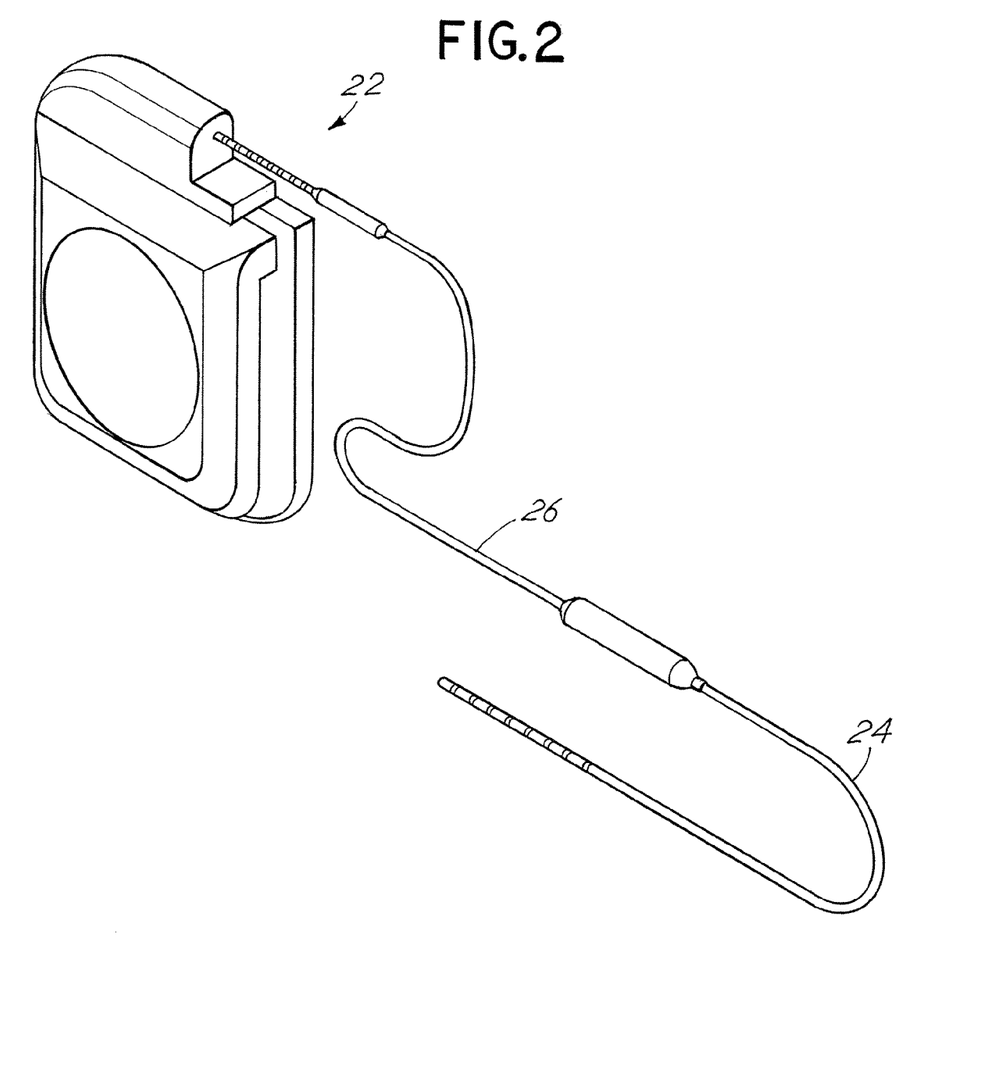
FIG. 2 shows an implantable medical device embodiment.
Figure 3:
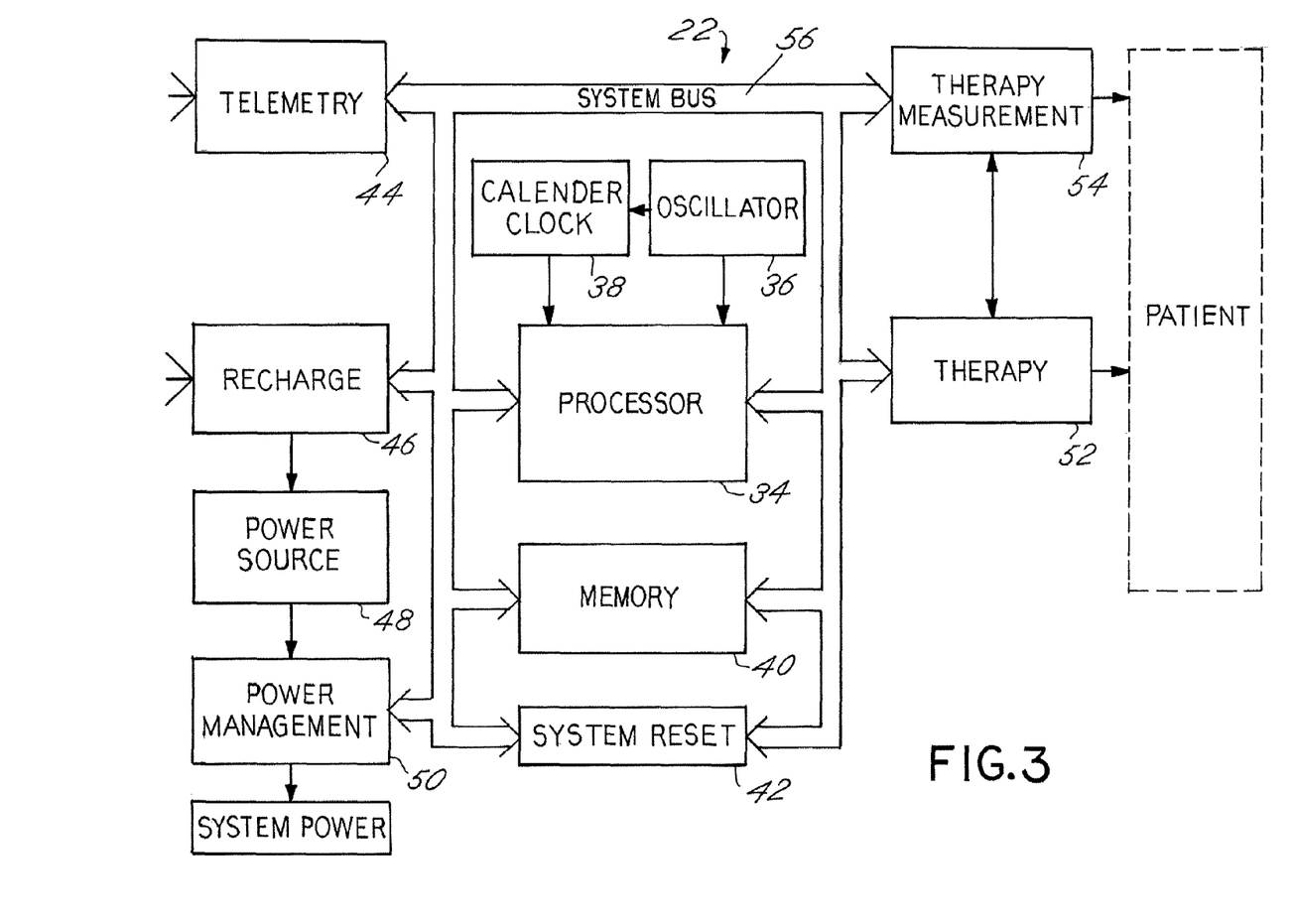
FIG. 3 shows an implantable medical device block diagram embodiment.

FIG. 2 shows an Implantable Neuro Stimulator (INS) 22 medical device embodiment 20. FIG. 3 shows a block diagram of the INS 22 embodiment. The INS 22 generates a programmable electrical stimulation signal. The INS 22 comprises a processor 34 with an oscillator 36, a calendar clock 38, memory 40, and system reset 42, a telemetry module 44, a recharge module 46, a power source 48, a power management module 50, a therapy module 52, and a therapy measurement module 54. Other versions of the INS 22 can include additional modules such as a diagnostics module. All components can be configured on one or more Application Specific Integrated Circuits (ASICs) except the power source 48. Also, all components are connected to bi-directional data bus 56 that is non-multiplexed with separate address and data lines except the oscillator 36, the calendar clock 38, and the power source 48. The processor 34 is synchronous and operates on low power such as a Motorola 68HC11 synthesized core operating with a compatible instruction set. The oscillator 36 operates at a frequency compatible with the processor 34, associated components, and energy constraints such as in the range from 100 KHz to 1.0 MHz. The calendar clock 38 counts the number of seconds since a fixed date for date/time stamping of events and for therapy control such as circadian rhythm linked therapies. The memory 40 includes memory 40 sufficient for operation of the INS such as volatile Random Access Memory (RAM) for example Static RAM, nonvolatile Read Only Memory (ROM), Electrically Eraseable Programmable Read Only Memory (EEPROM) for example Flash EEPROM, and register arrays configured on ASICs. Direct Memory Access (DMA) is available to selected modules such as the telemetry module 44, so the telemetry module 44 can request control of the data bus 56 and write data directly to memory 40 bypassing the processor 34. The system reset 42 controls operation of ASICs and modules during power-up of the INS 22, so ASICs and modules registers can be loaded and brought on-line in a stable condition. The INS 22 can be configured in a variety of versions by removing modules not necessary for the particular configuration and by adding additional components or modules. Primary cell, non-rechargeable, versions of the INS 22 will not include some or all of the components in the recharge module 46. All component of the INS 22 are contained within or carried on a housing that is hermetically sealed and manufactured from a biocompatible material such as titanium. Feedthroughs provide electrical connectivity through the housing while maintaining a hermetic seal, and the feedthroughs can be filtered to reduce incoming noise from sources such as cell phones. The INS 22 operates according to software parameters.

Figure 4:
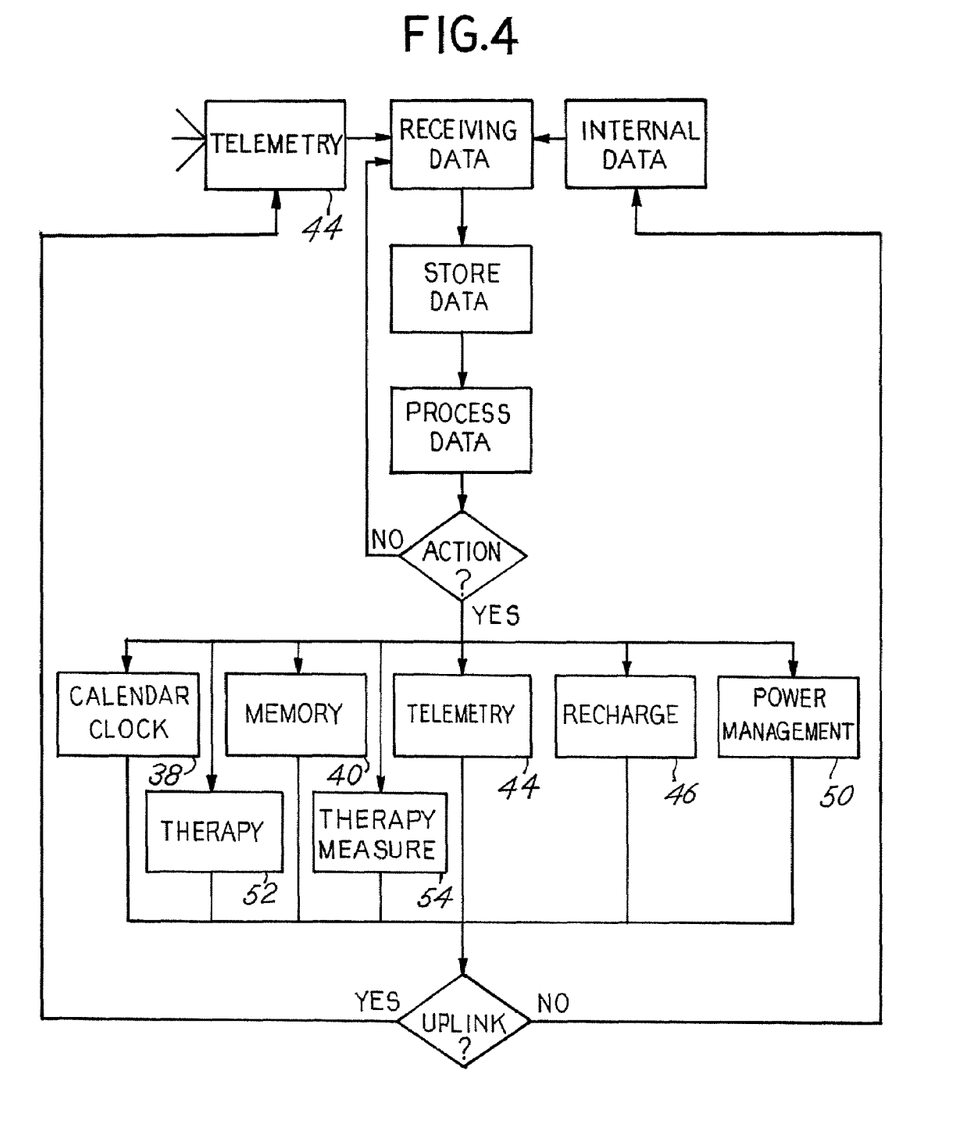
FIG. 4 shows an implatable medical device basic operation flowchart embodiment.

FIG. 4 shows a basic INS 22 operation flowchart embodiment. Operation begins with when the processor 34 receives data from either telemetry or from an internal source in the INS 22. The received data is then stored in a memory 40 location. The data is processed by the processor 34 to identify the type of data and can include further processing such as validating the integrity of the data. After the data is processed, a decision is made whether to take an action. If no action is required, the INS 22 stands by to receive data. If an action is required, the action will involve one or more of the following modules or components: calendar clock 38, memory 40, telemetry 44, recharge 46, power management 50, therapy 52, and therapy measurement 54. An example of an action would be to modify a programmed therapy. After the action is taken, a decision is made whether to prepare the action to be communicated, known as uplinked, to a programmer 30 through the telemetry module 44. If the action is uplinked, the action is recorded in the programmer. If the action is not uplinked, the action is recorded internally within the INS 22. An INS 22 as well as other implantable medical devices 20 can be configured with a telemetry module 44 having a telemetry processor.

Figure 5:
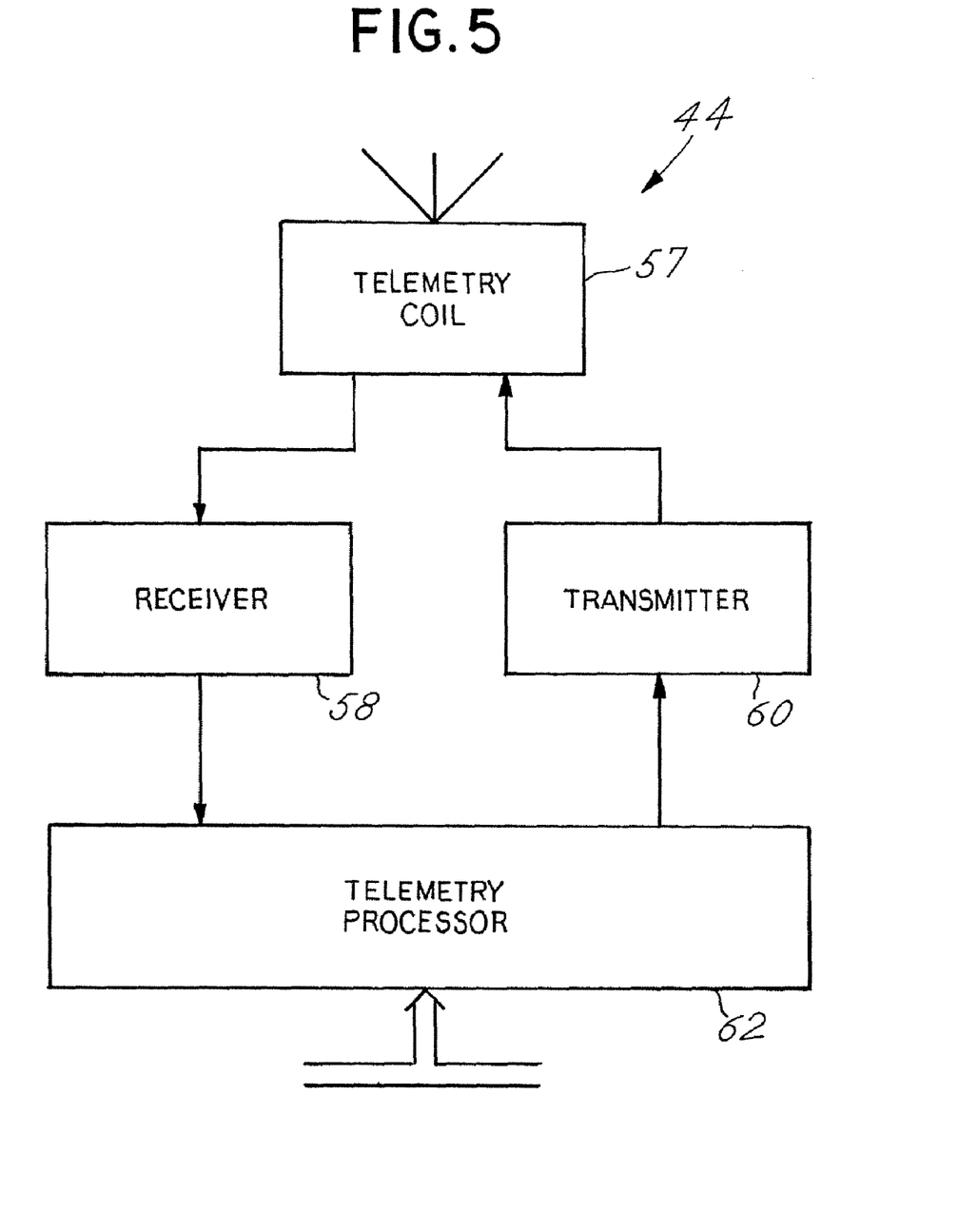
FIG. 5 shows a telemetry module block diagram embodiment.
Figure 6:
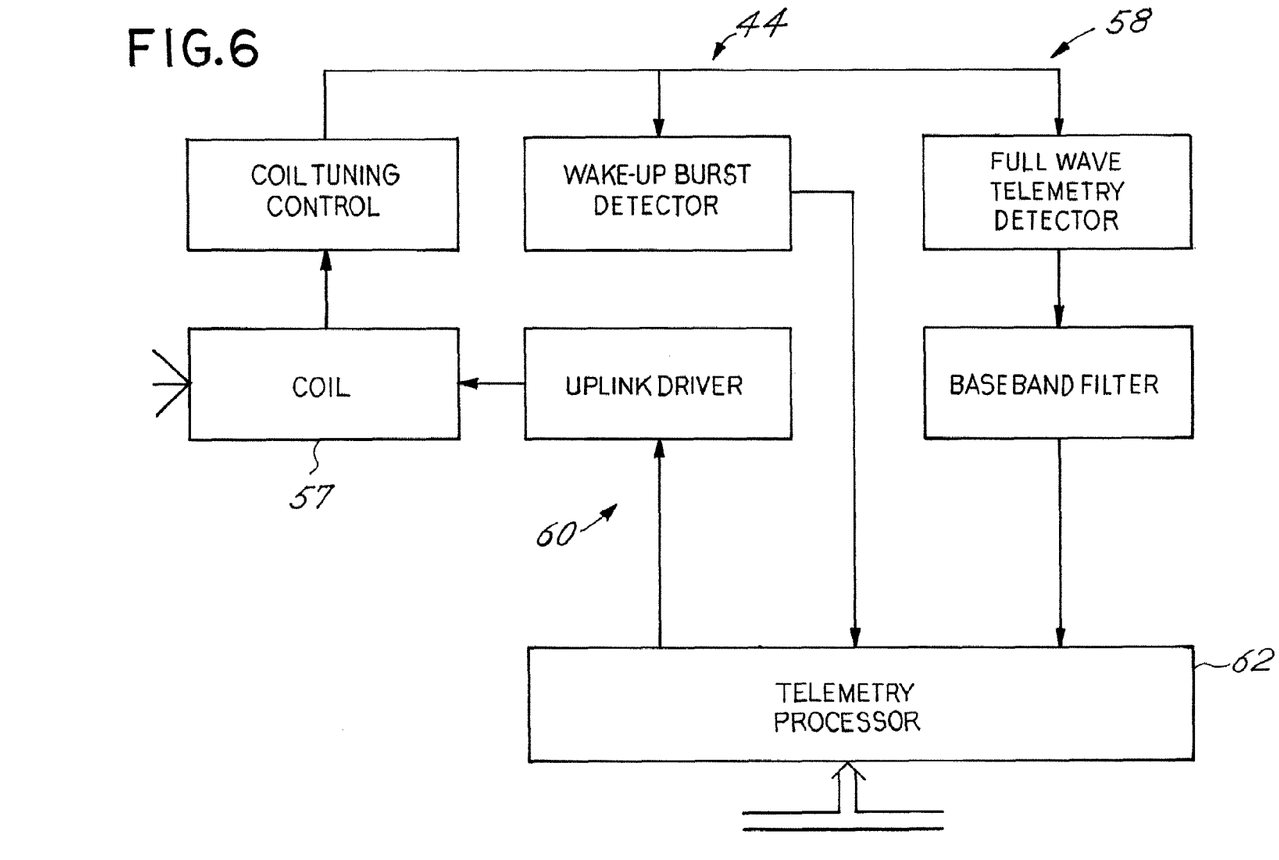
FIG. 6 shows a more detailed telemetry module block diagram embodiment.

FIGS. 5 and 6 show block diagrams of a telemetry module 44 embodiment. The telemetry module 44 provides bi-directional communications between the implantable medical device 20, also known as the uplink transmitter, and the programmer 30, also known as the downlink transmitter. The telemetry module 44 comprises a telemetry coil 57, a receiver 58, a transmitter 60, and a telemetry processor 62. Telemetry is conduced at a frequency in the range from about 150 KHz to 200 KHz using a medical device 20 protocol such as described in U.S. Pat. No. 5,752,977 "Efficient High Data Rate Telemetry Format For Implanted Medical Device" issued to Grevious et al. (May 19, 1998). The telemetry coil 57 can be located inside the housing or attached to the outside of the housing, and the telemetry coil 57 can also function as the recharge coil if operation of the coil is multiplexed. The receiver 58 provides a digital pulse representing the Radio Frequency (RF) modulated signal, knows as a downlink signal, from a programmer 30. The transmitter 60 generates an RF modulated uplink signal from the digital signal generated by the telemetry processor 62. The telemetry processor 62 can by a state machine configured on an ASIC with the logic necessary to decode telemetry signals during reception, store data into RAM, and notify the processor 62 that data was received. The telemetry processor 62 also provides the logic necessary during transmission to request the main processor 34 to read data from RAM, encode the data for transmission, and notify the main processor 34 that the data was transmitted.

Figure 7:
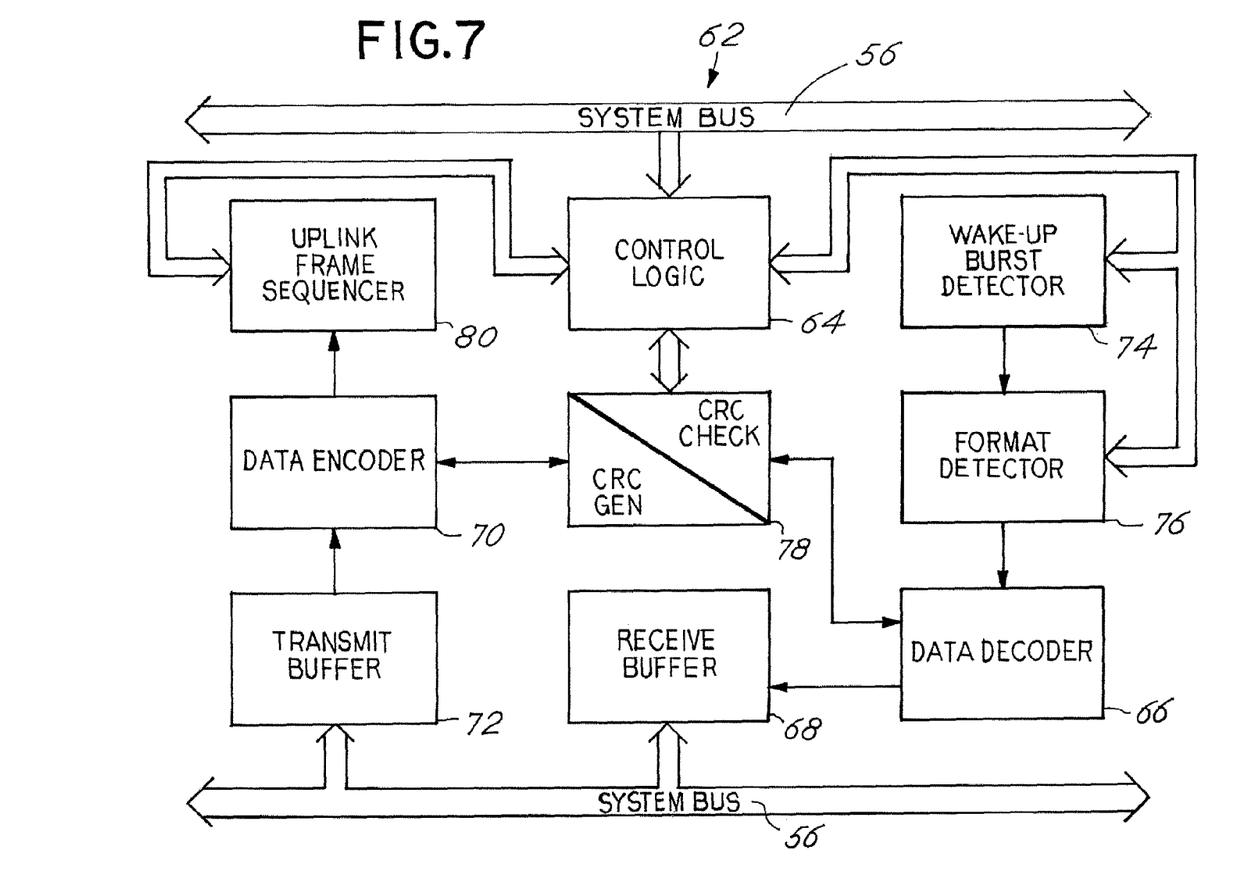
FIG. 7 shows a telemetry processor block diagram embodiment.

FIG. 7 shows a block diagram of a telemetry processor 62 embodiment. The telemetry processor 62 comprises control logic 64, a data decoder 66, a receive buffer 68, a data encoder 70, and a transmit buffer 72. The control logic 64 operates the telemetry processor 62 according to telemetry parameters. The telemetry parameters can be configured in telemetry processor 62 hardware parameters, firmware parameter, or a combination of hardware parameters and firmware parameters. Hardware parameters can be configured in registers contained within the telemetry processor. The data decoder 66 is coupled to the control logic 64 and coupleable to a demodulator. The data decoder 66 translates a received serial bit stream into parallel accessible words. The data decoder 66 can also be coupleable to the main processor bus 56 to receive protocol control data from the main processor 34. The receive buffer 68 is coupled to the data decoder 66 and coupleable to a main processor bus 56. The receive buffer 68 is used to assemble the received message to be processed by the telemetry processor 62 and communicated to the main processor 34. The data encoder 70 is coupled to the control logic 64 and coupleable to a modulator. The data encoder 70 translates parallel accessible words into a serial bit stream for transmission. The data encoder 70 can also be coupleable to the main processor bus 56 to receive status data from the main processor 34. The transmit buffer 72 is coupled to the data encoder 70 and coupleable to the main processor bus 56. The transmit buffer 72 is used for communicating a message from the main processor 34 to the telemetry processor 62.

In some embodiments, the telemetry processor 62 can also include a wake-up detector 74, a format detector 76, cycle redundancy check logic 78, and an uplink frame sequencer 80. The wake-up detector 74 is coupled to the format detector 76 and coupleable to the demodulator. The wake-up detector 74 powers-up the telemetry processor 62 upon reception of a wake-up burst. With a wake-up detector 74, the telemetry processor 62 can idles in a sleep mode that consumes very low power such as less than 1% of the power used by the telemetry processor 62 when the telemetry processor 62 has been activated by a wake-up burst. A format detector 76 is coupled to the data decoder 66 and coupleable to a demodulator. The format detector 76 identifies the telemetry format being received, and the format detector 76 switches the telemetry processor 62 to the appropriate telemetry format for the modulation and speed of the downlink transmission. Cyclic redundancy check logic 78 is coupled to the data decoder 66. The cycle redundancy check logic 78 compares a downlink check number against a downlink message to detect whether the downlink message has the correct number of data bits and correct order of the data bits. An uplink frame sequence generator 80 is coupled to the data encoder 70. The uplink frame sequencer 80 adds an uplink header to each uplink message containing information such as a source address, a destination address, frame sequence number, status information, and the like. The source address is the programmer 30 address that is identified to ensure the implantable device 20 is receiving information from the appropriate programmer 30 and that the programmer 30 has current information from the implantable medical device 20. The destination address is the implantable medical device 20 address that is identified to ensure the correct implantable medical device 20 is receiving the transmission. The destination address is particularly important when a patient has more than one implantable medical device 20 to ensure the correct implantable medical device 20 is receiving the downlink signal. The frame sequence number allows the telemetry processor 62 to identify duplicate transmissions of the same command message. Duplicate command messages can occur in situations such as when a movement disorder patient unintentionally actuates patient programmer 34 controls multiple times, or when a programming wand is swiped multiple times across the location of the medical device 20. When a duplicate command message is identified, the duplicate message is typically ignored by the telemetry processor 62. The status information provides data on the status of the communications link between the programmer 30 and implantable medical device 20, and data on the status of the implantable medical device 20 such as whether memory 40 has been corrupted, whether there has been a Power On Reset (POR), and the like.

All messages received by and transmitted from the implantable medical device 20 are processed at least partially by the telemetry processor 62 without main processor 34 involvement. The telemetry processor 62 processes selected messages faster and with less energy than messages processed by the main processor 34. Selected messages can also be processed by the telemetry processor 62 when the main processor 34 is inoperative. The selected messages include acknowledgement (ACK) messages negative acknowledgement (NACK) messages, and handshake command messages. The telemetry processor 62 can process an entire handshake message between a programmer 30 and a medical device 20 that includes the handshake command message and the acknowledgement message or negative acknowledgement message without main processor 34 assistance. The handshake message can also include link status and medical device 20 status information that is also processed by the telemetry processor 62 without main processor 34 assistance. Handshake messages typically occur periodically to report communications link status between the programmer 30 and the medical device 20. When handshaking, the telemetry processor 62 typically begins transmission of an acknowledgement message or a negative acknowledgement message in less than 500.0 µSec such as in the range from 100.0 µSec to 500.0 µSec after the command message is received. Some embodiments of the telemetry processor 62 can also operate in at least two different modes of communication.

In the direct mode of communication, the telemetry processor 62 operates upon a single message transmitted by either the programmer 30 or the implantable medical device 20 and a single acknowledgement transmitted by the receiving device. When using the direct mode of communications, the programmer 30 is first set typically by the patient, and then the programmer 30 is brought close enough to the implantable medical device 20 for brief communications. The direct mode of communication is used for communications such as incrementing therapy parameters such as stimulation amplitude. The direct mode of communication facilitates brief communications such as in the range from 50.0 mSec to 150.0 mSec from the time the downlink device begins communications until the communications have been completed. Brief communications can be useful when the programmer 30 is a device such as a programming wand that programs the medical device 20 with a momentary swipe across the location of the medical device 20. With the direct mode of communications, the programmer 30 can be substantially in motion during communications. Duplicate transmission of the same command message can occur during the direct mode of communication when, for example, a programming wand is swiped multiple times across the location of the medical device 20. The telemetry processor 62 can ignore duplicate command messages by identifying that the frame sequence number in the message header is out of sequence.

In the session mode of communications, there is continual handshaking to quickly detect a break in telemetry. The session mode is used for more complex communications between the uplink transmitter and the medical device 20 such as large memory 40 transfers that include data, programs, or both, The programmer 30 is typically held substantially static while communications are conducted in the secession mode. The telemetry processor 62 ignores subsequent transmissions of the same command message just as in the direct mode of communications.

Figure 8:
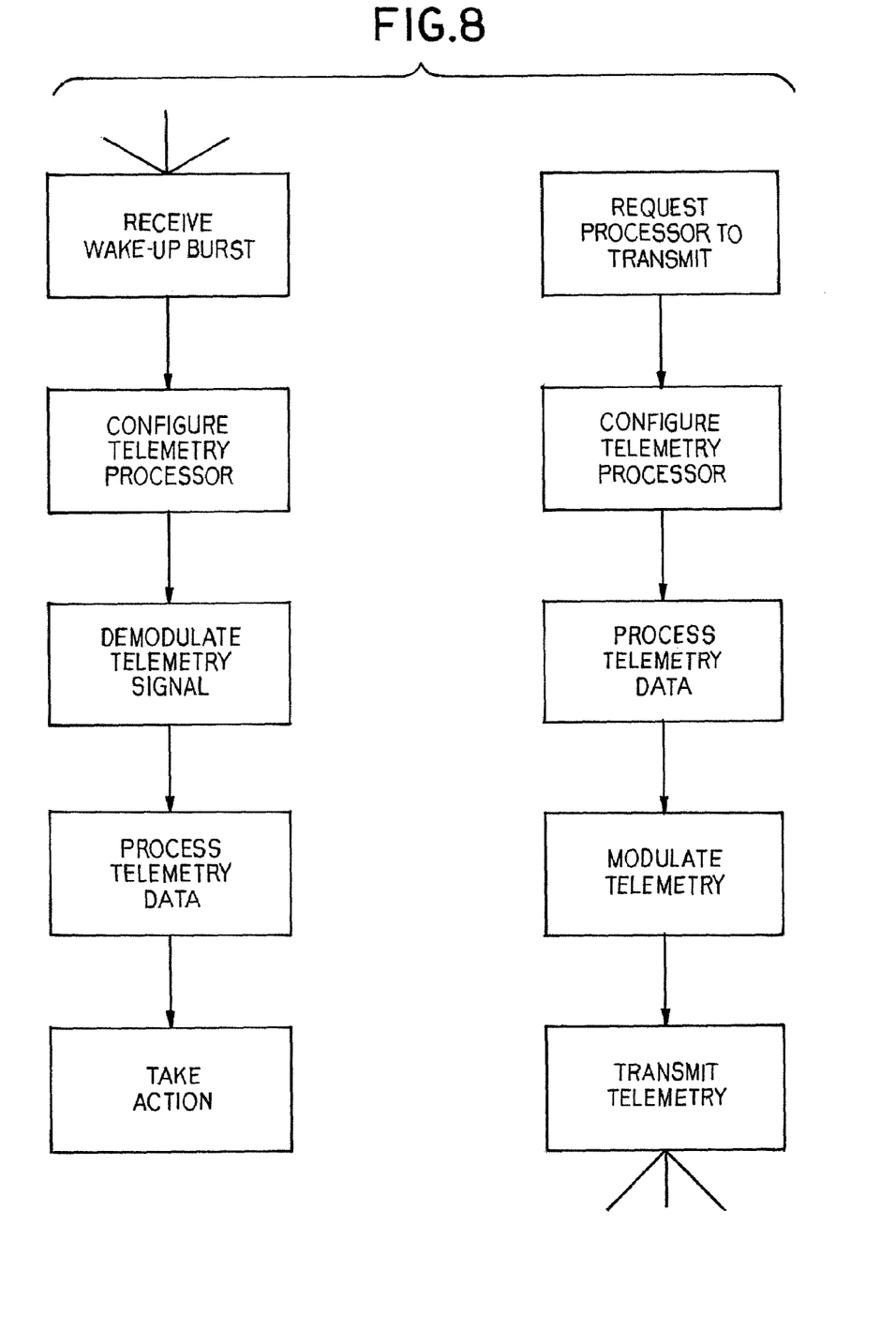
FIG. 8 shows a telemetry module operation flowchart embodiment.

FIG. 8 shows a telemetry module 44 operation flowchart embodiment. To begin telemetry, either the patient or the clinician uses a patient programmer 34 or console programmer 32 and places the telemetry head containing the telemetry coil 57 near the implantable medical device 20. Both the console programmer 32 and patient programmer 34 can have an antenna locator that indicates when the telemetry head is aligned closely enough with the implanted medical device 20 for adequate telemetry. The RF telemetry signal is received through the telemetry coil 57 and includes a wake-up burst that signals the telemetry processor 62 to prepare the telemetry processor 62 to receive incoming telemetry signals. The telemetry processor 62 is configured to receive a particular telemetry protocol that includes the type of telemetry modulation and the speed of the incoming telemetry signal. The telemetry receiver 58 demodulates the time base signal into digital pulses. The telemetry processor 62 converts the digital pulses into binary data that is stored into memory 40. The main processor 34 will then take whatever action is directed by the received telemetry such as adjusting the therapy. Telemetry signal transmission is initiated by the main processor 34 requesting the telemetry processor 62 to transmit data The telemetry processor 62 is configured for the desired telemetry protocol that includes the type of modulation and the speed for transmission. The telemetry processor 62 converts binary data desired to be transmitted into a time based digital pulses. The transmitter 60 modulates the digital signal into an RF signal that is then transmitted through the telemetry coil 57 to a programmer 30.

Figure 9:
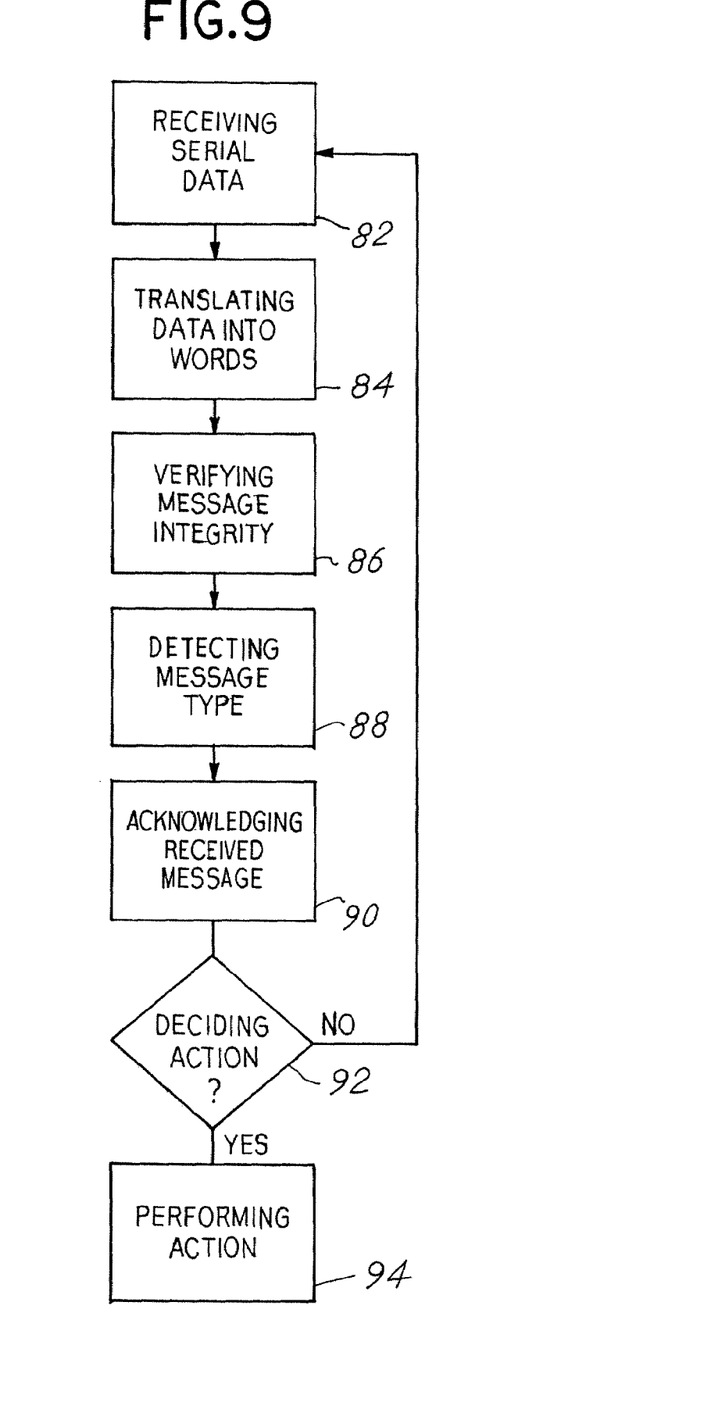
FIG. 9 shows a telemetry reception flowchart embodiment.
Figure 10:
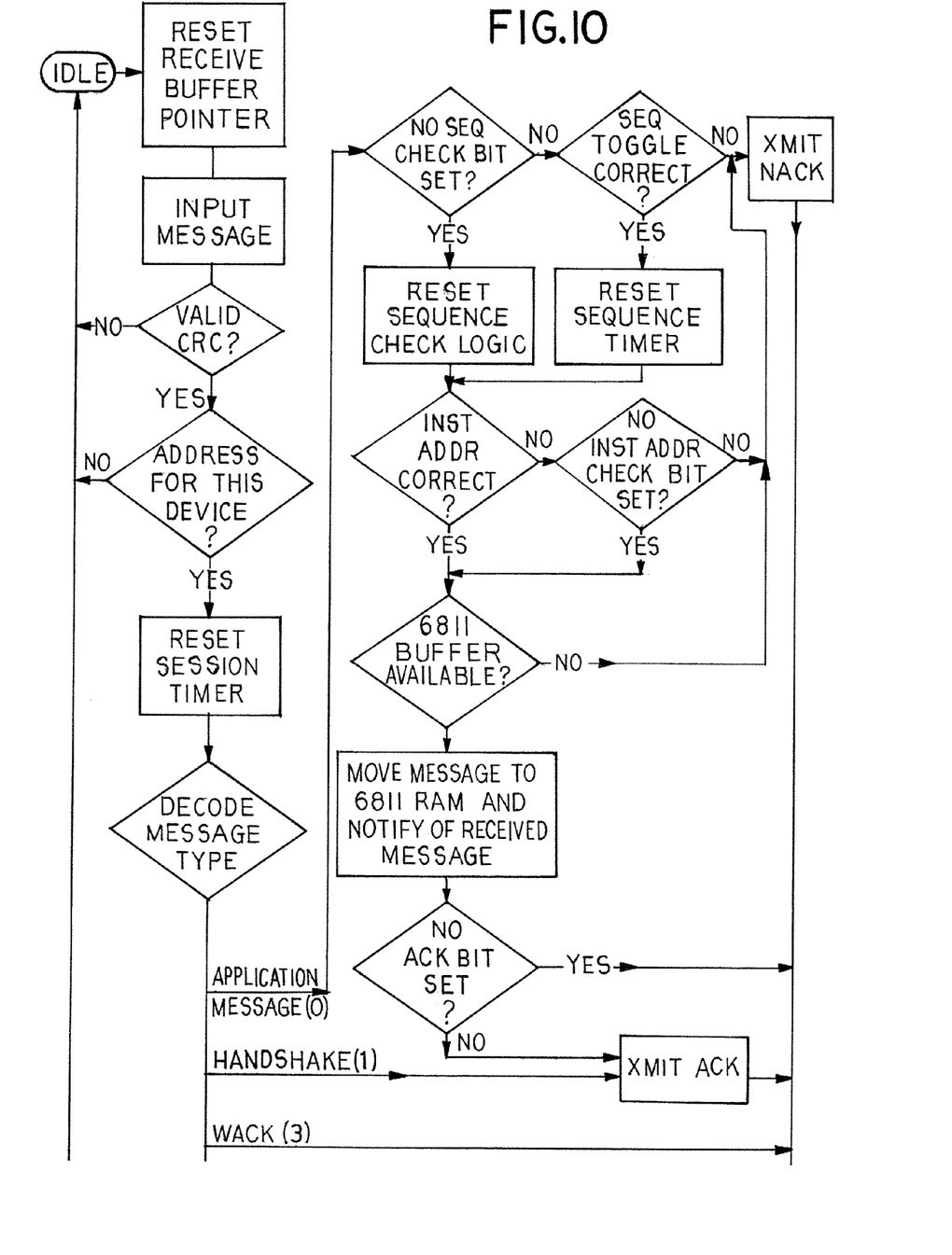
FIG. 10 shows a telemetry reception more detailed flowchart embodiment.

FIGS. 9 and 10 show telemetry reception flowchart embodiments. The method of processing received telemetry signals in an implantable medical device 20 comprises the following steps that are not necessarily described in order. A serial data stream is received 82 from the demodulator. The received serial data stream is translated 84 into parallel accessible words. The message's integrity is verified 86. Message integrity verification typically includes determining whether the message address has a valid Cycle Redundancy Check (CRC) and whether the message is intended for the receiving implantable medical device. To determine if the message is intended for the implantable medical device, the destination address is checked, the source address is checked, and the sequence number is checked to determine if the message is out of sequence. If the message has a valid CRC, destination address, source address, and sequence number, then the telemetry processor replies with an acknowledgement message. If the message has a valid CRC but not a valid destination address, or source address or sequence number, then the telemetry processor replies with a negative acknowledgement message. If the CRC is not valid, then the telemetry processor does not reply because without a valid CRC the received signal can be noise.

After message integrity is verified 86, the message type is detected 88. The message can be a variety of types including an application message, a handshake message, and a Waveform ACKnowledgement (WACK) message. If the message is an application message, then an acknowledgement is sent 90 to the transmitter of the message. If the message is a handshake message, then an acknowledgement is sent 90 to the transmitter of the handshake message. If the message is a WACK message, then the WACK provides its own handshaking during waveform uplinking. Next the message is accessed to decide 92 whether an action is required. If an action is required, then the action is performed 94, and if an action is not required then the telemetry processor stands-by to receive more serial data.

In some embodiments, the method of processing received telemetry signals in an implantable medical device 20 can also include the following steps. A wake-up burst is received that activates the telemetry processor 62. Also the incoming data stream can be shifted through the cycle redundancy check logic 78 for the cycle redundancy check logic 78 to verify that a complete message has been received. The cycle redundancy check logic 78 compares a downlink check number against a downlink message to detect whether the downlink message has the correct number of data bit and correct order of the data bits. Additionally, a format detector 76 can be coupled to the data decoder 66 and the demodulator to detect the telemetry format being received. The main processor 34 can be notified when an application message has been received.

Figure 11:
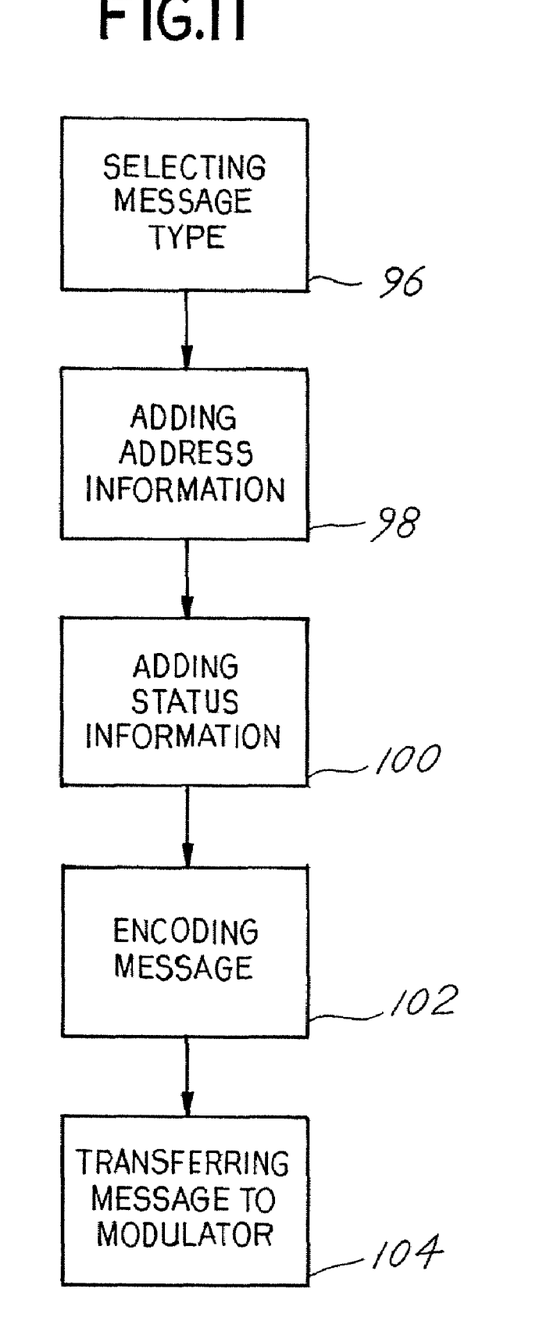
FIG. 11 shows a telemetry transmission flowchart embodiment.
Figure 12:
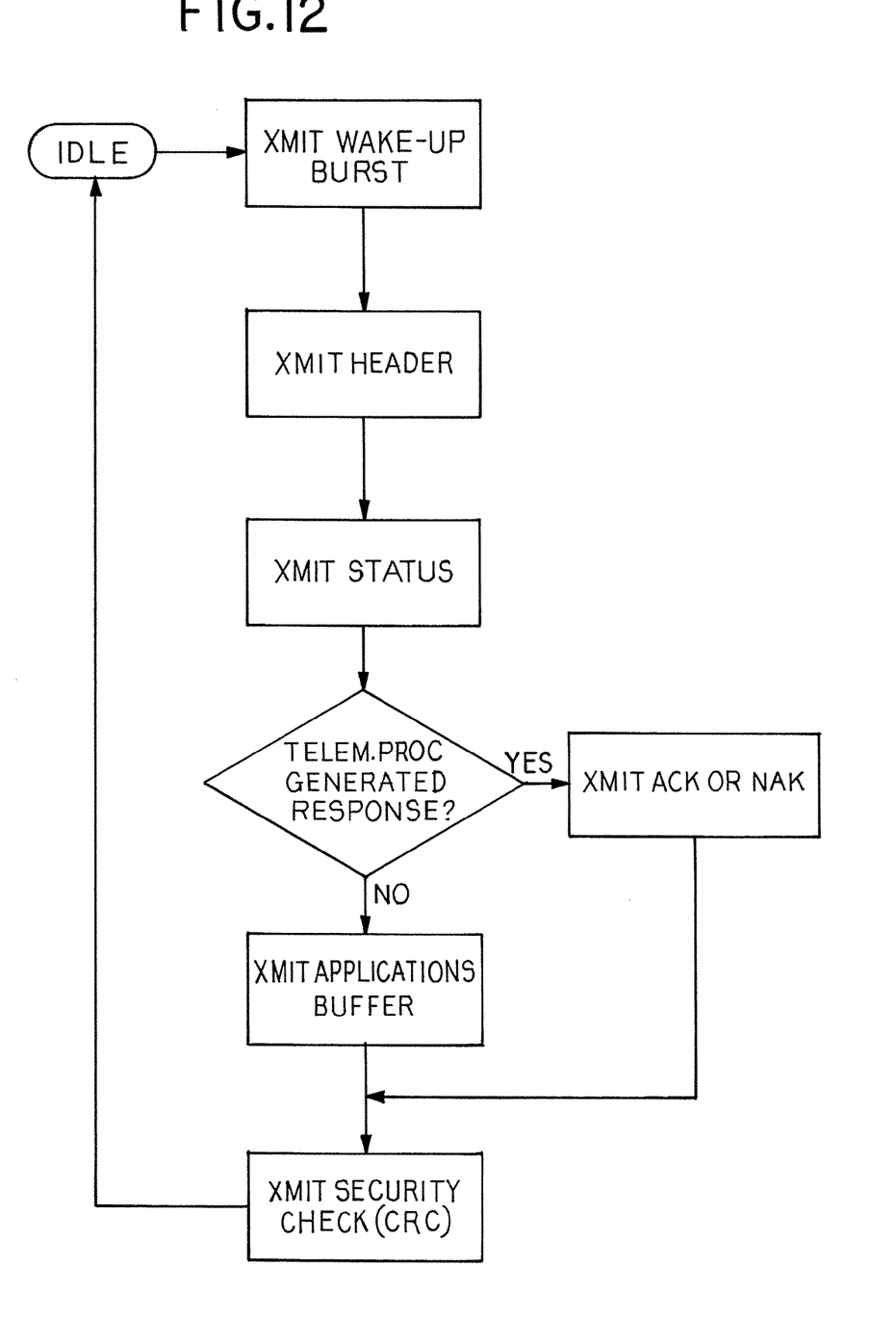
FIG. 12 shows a telemetry transmission more detailed flowchart embodiment.

FIGS. 11 and 12 show telemetry transmission flowchart embodiments. The method of processing transmitted telemetry signals in an implantable medical device 20 comprises the following steps that are not necessarily described in order. The message type to be transmitted is selected with control logic 96. The message type transmitted can be an acknowledgement, negative acknowledgement, application, and waveform. The buffer is specified where the message to be transmitted is located. Message uplink header information including source address, destination address, and frame sequence number is added 98 with an uplink frame generator 80, and status information is added 100 with control logic 64. The transmit message is encoded 102 in parallel accessible words into transmit message serial data bits. The message is transferred 104 to a modulator for transmission by telemetry.

In some embodiments, the following additional steps can be included in the method of processing transmitted telemetry messages. A validity code can be generated containing the number of transmit data bits and the order of the transmit data bits. The validity code is typically added to the message trailer. The application program can be notified that the message has been transmitted. After the message is transferred to the modulator, the telemetry processor 62 can be powered down. A status message can be sent from the main processor 34 to the data encoder 70.

Thus, embodiments of an implantable medical device 20 with telemetry processor 62 are disclosed provide benefits such as reducing demands on the main processor to free the main processor for other tasks, conserving energy, increasing telemetry processing speed, and many other advantages apparent from the claims. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A method of processing transmitted telemetry signals in an implantable medical device including a main processor and a telemetry processor, the method comprising:
    selecting a message type to be transmitted with control logic;
    adding source and destination address information with an uplink frame generator;
    adding status information with control logic;
    encoding a transmit message parallel accessible words into a transmit message serial data bits; and
    transferring the message to a modulator for transmission of the message by telemetry, wherein the above steps are performed in the telemetry processor distinct from the main processor of the implantable medical device to adjust therapy based on the received message.

2. The method as in claim 1, further comprising generating message validity code containing the number of transmit data bits and the order of the transmit data bits with a cyclic redundancy check generator.

3. The method as in claim 1, further comprising powering down the telemetry processor after transferring the message to a modulator.

4. The method as in claim 1, further comprising sending a status message from the main processor to a data encoder.

5. A method of processing transmitted telemetry signals in an implantable medical device including a main processor and a telemetry processor, the telemetry processor executing the steps comprising:
    selecting a message type to be transmitted with control logic;
    adding source and destination address information with an uplink frame generator;
    adding status information with control logic;
    generating message validity codes including the number of transmit data bits and an order of the transmit data bits with a cyclic redundancy check generator;

encoding the transmit message parallel accessible words into a transmit message serial data bits;

transferring a message to a modulator for transmission of the message by telemetry, and powering down the telemetry processor after transferring the message to the modulator.

* * * * *

UNITED STATES PATENT AND TRADEMARK OFFICE
CERTIFICATE OF CORRECTION

PATENT NO.      : 7,610,099 B2                                          Page 1 of 1
APPLICATION NO. : 11/463782
DATED           : October 27, 2009
INVENTOR(S)     : Almendinger et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 575 days.

Signed and Sealed this

Twelfth Day of October, 2010

David J. Kappos
*Director of the United States Patent and Trademark Office*